(12) United States Patent
Zhang et al.

(10) Patent No.: US 10,285,952 B2
(45) Date of Patent: May 14, 2019

(54) NANOPARTICLES LEVERAGE BIOLOGICAL MEMBRANES TO TARGET PATHOGENS FOR DISEASE TREATMENT AND DIAGNOSIS

(71) Applicant: The Regents of the University of California, Oakland, CA (US)

(72) Inventors: Liangfang Zhang, San Diego, CA (US); Che-Ming Jack Hu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/000,110

(22) Filed: Jan. 19, 2016

(65) Prior Publication Data
US 2016/0136106 A1     May 19, 2016

Related U.S. Application Data

(63) Continuation of application No. PCT/US2014/050355, filed on Aug. 8, 2014.
(Continued)

(51) Int. Cl.
| | |
|---|---|
| *A61K 9/00* | (2006.01) |
| *A61K 9/51* | (2006.01) |
| *A61K 9/50* | (2006.01) |
| *A61K 35/17* | (2015.01) |
| *A61K 35/18* | (2015.01) |

(Continued)

(52) U.S. Cl.
CPC .......... *A61K 9/5176* (2013.01); *A61K 9/5094* (2013.01); *A61K 9/51* (2013.01); *A61K 9/5153* (2013.01); *A61K 31/4709* (2013.01); *A61K 35/17* (2013.01); *A61K 35/18* (2013.01); *A61K 35/19* (2013.01); *A61K 49/00* (2013.01);
(Continued)

(58) Field of Classification Search
CPC ...................................................... A61K 9/5176
See application file for complete search history.

(56) References Cited

U.S. PATENT DOCUMENTS

| | | | |
|---|---|---|---|
| 5,358,722 A | 10/1994 | Monzyk | |
| 5,491,219 A | 2/1996 | Mann | |

(Continued)

FOREIGN PATENT DOCUMENTS

| | | | |
|---|---|---|---|
| CN | 1798548 A | 7/2006 | |
| CN | 10306196 A | 11/2008 | |

(Continued)

OTHER PUBLICATIONS

PCT International Search Report and Written Opinion for PCT Application No. PCT/US2014/050355 dated Nov. 13, 2014 (9 pages).

(Continued)

*Primary Examiner* — Paul W Dickinson
(74) *Attorney, Agent, or Firm* — Eversheds Sutherland (US) LLP

(57) ABSTRACT

Provided are methods, combinations and pharmaceutical compositions for treating or preventing an infection in a subject using a nanoparticle comprising a) an inner core comprising a non-cellular material, and b) an outer surface comprising a cellular membrane configured for adhesion of a pathogen that causes said infection. Exemplary infection includes infection caused by a virus, bacterium, fungus, or protozoan.

12 Claims, 2 Drawing Sheets

Related U.S. Application Data

(60) Provisional application No. 61/863,528, filed on Aug. 8, 2013.

(51) Int. Cl.
  *A61K 35/19* (2015.01)
  *A61K 31/4709* (2006.01)
  *A61K 49/00* (2006.01)
  *G01N 33/569* (2006.01)
  *G01N 33/58* (2006.01)

(52) U.S. Cl.
  CPC ..... *G01N 33/56905* (2013.01); *G01N 33/587* (2013.01); *G01N 2333/445* (2013.01)

(56) References Cited

U.S. PATENT DOCUMENTS

| | | | |
|---|---|---|---|
| 5,718,915 | A | 2/1998 | Virtanen et al. |
| 8,846,026 | B2 | 9/2014 | Plebanski |
| 2004/0110695 | A1 | 6/2004 | Dobbie et al. |
| 2005/0118275 | A1 | 6/2005 | O'Hagan |
| 2006/0292174 | A1 | 12/2006 | de los Rios et al. |
| 2007/0243137 | A1 | 10/2007 | Hainfeld et al. |
| 2007/0258889 | A1 | 11/2007 | Douglas et al. |
| 2009/0163540 | A1* | 6/2009 | Sun .............. C07D 453/04 514/305 |
| 2009/0214663 | A1 | 8/2009 | Albrecht et al. |
| 2009/0274630 | A1 | 11/2009 | Huang |
| 2010/0021503 | A1 | 1/2010 | Denoel et al. |
| 2010/0028994 | A1 | 2/2010 | DeSimone et al. |
| 2011/0262415 | A1 | 10/2011 | Grimaldi et al. |
| 2011/0280930 | A1 | 11/2011 | Batista et al. |
| 2013/0337066 | A1 | 12/2013 | Zhang et al. |
| 2016/0136106 | A1 | 5/2016 | Zhang et al. |
| 2017/0000875 | A1 | 1/2017 | Hu |
| 2017/0079909 | A1 | 3/2017 | Zhang et al. |
| 2017/0095510 | A1 | 4/2017 | Lee |
| 2017/0274059 | A1 | 9/2017 | Zhang et al. |

FOREIGN PATENT DOCUMENTS

| | | |
|---|---|---|
| CN | 101735613 A | 6/2010 |
| GB | 2482069 A | 1/2012 |
| JP | 2005/525407 A | 8/2008 |
| RU | 2345805 C1 | 2/2009 |
| WO | 2005020964 A1 | 3/2005 |
| WO | 2008/003524 A2 | 1/2008 |
| WO | 2008/013952 A2 | 1/2008 |
| WO | 2008/150276 A2 | 12/2008 |
| WO | 2010/070620 A1 | 6/2010 |
| WO | 2011002239 A2 | 6/2011 |
| WO | 2011/116219 A1 | 9/2011 |
| WO | 2013/052167 A2 | 4/2013 |
| WO | 2015021390 A2 | 2/2015 |
| WO | 2015/187502 A1 | 12/2015 |
| WO | 2016/109306 A1 | 7/2016 |
| WO | 2016/153979 A1 | 9/2016 |
| WO | 2016/176041 A1 | 11/2016 |
| WO | 2016/205009 A1 | 12/2016 |
| WO | 2016/205010 A1 | 12/2016 |
| WO | 2017/087897 A1 | 5/2017 |

OTHER PUBLICATIONS

Sahoo SK, Labhasetwar V. Enhanced anti proliferative activity of transferrin-conjugated paclitaxel-loaded nanoparticles is mediated via sustained intracellular drug retention. Mol. Pharm. 2(5), 373-383 (2005).

Cho, Nam-Hyuk et al. "A Multifunctional Core-Shell Nanoparticle for Dendritic Cell-Based Cancer Immunotherapy." Nature Nanotechnology: 6, 675-82 (2011).

Li, Haiyan et al. "Alpha-Alumina Nanoparticles Induce Efficient Autophagy-Dependent Cross-Presentation and Potent Antitumour Response." Nature Nanotechnology 6, 645-650 (2011).

Moon, James J et al. "Interbilayer-Crosslinked Multilamellar Vesicles as Synthetic Vaccines for Potent Humoral and Cellular Immune Responses." Nature Materials 10.3 (2011): 243-251.

Tongchusak, S et al. "Induction of Anti-Tumor Cytotoxic T Cell Responses Through PLGA-Nanoparticle Mediated Antigen Delivery." Biomaterials (2011), 32(14):3666-78.

A. E Clatworthy, E Pierson, D. T. Hung, Targeting virulence: a new paradigm for antimicrobial therapy. Nat Chem Biol 3, 541 (Sep. 2007).

D. G. Beghini et al., Anti-sera raised in rabbits against crotoxin and phospholipase A2 from Crotalus durissus cascavella venom neutralize the neurotoxicity of the venom and crotoxin. Toxicon 44, 141 (Aug. 2004).

Z. Chen et al., Potent neutralization of anthrax edema toxin by a humanized monoclonal antibody that competes with calmodulin for edema factor binding. Proc Natl Acad Sci U S A 106, 13487 (Aug. 11, 2009).

W. W. Kum, A. W. Chow, Inhibition of staphylococcal enterotoxin A-induced superantigenic and lethal activities by a monoclonal antibody to toxic shock syndrome toxin-1. J Infect Dis 183, 1739 (Jun. 15, 2001).

C. C. McCormick, A. R. Caballero, C. L. Balzli, A. Tang, R. J. O'Callaghan, Chemical inhibition of alpha-toxin, a key corneal virulence factor of *Staphylococcus aureus*. Invest Ophthalmol Vis Sci 50, 2848 (Jun. 2009).

D. T. Hung, E. A. Shakhnovich, E. Pierson, J. J. Mekalanos, Small-molecule inhibitor of Vibrio cholerae virulence and intestinal colonization. Science 310, 670 (Oct. 28, 2005).

Y. Hoshino et al., The rational design of a synthetic polymer nanoparticle that neutralizes a toxic peptide in vivo. Proc Natl Acad Sci U S A 109, 33 (Jan. 3, 2012).

Y. Hoshino et al., Recognition, neutralization, and clearance of target peptides in the bloodstream of living mice by molecularly imprinted polymer nanoparticles: a plastic antibody. J Am Chem Soc 132, 6644 (May 19, 2010).

R. J. Gilbert, Pore-forming toxins. Cell Mol Life Sci 59, 832 (May 2002).

C. J. Rosado et al., The MACPF/CDC family of pore-forming toxins. Cell Microbiol 10, 1765 (Sep. 2008).

J. Bubeck Wardenburg, O. Schneewind, Vaccine protection against *Staphylococcus aureus* pneumonia. J Exp Med 205, 287 (Feb. 18, 2008).

M. Shoham, Antivirulence agents against MRSA. Future Med Chem 3, 775 (May 2011).

P. O'Hanley, G. Lalonde, G. Ji, Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis. Infect Immun 59, 1153 (Mar. 1991).

B. T. Edelson, E. R. Unanue, Intracellular antibody neutralizes Listeria growth. Immunity 14, 503 (May 2001).

B. T. Edelson, P. Cossart, E. R. Unanue, Cutting edge: paradigm revisited: antibody provides resistance to Listeria infection. J Immunol 163, 4087 (Oct. 15, 1999).

A. Nakouzi, J. Rivera, R. F. Rest, A. Casadevall, Passive administration of monoclonal antibodies to anthrolysin O prolong survival in mice lethally infected with Bacillus anthracis. BMC Microbiol 8, 159 (2008).

J. E. Alexander et al., Immunization of mice with pneumolysin toxoid confers a significant degree of protection against at least nine serotypes of *Streptococcus pneumoniae*. Infect Immun 62, 5683 (Dec. 1994).

L. A. Kirkham et al., Construction and immunological characterization of a novel nontoxic protective pneumolysin mutant for use in future pneumococcal vaccines. Infect Immun 74, 586 (Jan. 2006).

I. Andreeva-Kovalevskaya Zh, A. S. Solonin, E V. Sineva, V. I. Ternovsky, Pore-forming proteins and adaptation of living organisms to environmental conditions. Biochemistry (Mosc) 73, 1473 (Dec. 2008).

(56) References Cited

OTHER PUBLICATIONS

G. Ma, Q. Cheng, Vesicular polydiacetylene sensor for colorimetric signaling of bacterial pore-forming toxin. Langmuir 21, 6123 (Jul. 5, 2005).
D. Pornpattananangkul et al., Bacterial toxin-triggered drug release from gold nanoparticle-stabilized liposomes for the treatment of bacterial infection. J Am Chem Soc 133, 4132 (Mar. 23, 2011).
D. Branton et al., The potential and challenges of nanopore sequencing. Nat Biotechnol 26, 1146 (Oct. 2008).
Goshi K, Cluff L, Johnson J. "Studies on the Pathogenesis of Staphylococcal Infection." The Journal of Experimental Medicine. 1961, 113(2): 259-270.
Ragle, B.E. et al. "Anti-Alpha-Hemolysin Monoclonal Antibodies Mediate Protection against *Staphylococcus aureus* Pneumonia." Infection and Immunity. 2009, 77(7):2712-2718.
Wardenburg B, Schneewind O., "Vaccine protection against *Staphylococcus aureus* pneumonia." The Journal of Experimental Medicine. 2008, 205(2): 287-294.
A. S. Klainer et al., Staphylococcal Alpha-Hemolysin: Detection on the Erythrocyte Membrane by Immunofluorescence. Science, vol. 145, No. 3633, pp. 714-715 (Aug. 14, 1964).
Chinese Office Action dated Feb. 2, 2015.
Jianlin Xu, Experimental Study on Magnetized Technique of Doxorubicin-loaded Erythrocytes, Wanfang Data, pp. 13, 21-22, 35, 52, Oct. 19, 2009.
Yoo et al. (Journal of Controlled release (2000), 68, 419-431).
International Preliminary Report on Patentability for PCT Application No. PCTUS2012/039411 dated Apr. 3, 2014 (6 pages).
Antonelli et al., 2011, "Encapsulation of Superparamagnetic Nanoparticles into Red Blood Cells as New Carriers of MRI Contrast Agents," Nanomedicine, 6(2):211-223.
Antonelli et al., 2008, "New Biomimetic Constructs for Improved In Vivo Circulation of Superparamagnetic Nanoparticles," Nanoscience and Nanotechnology, 8(5):2270-2278.
Brahler et al., 2006, "Magnetite-Loaded Carrier Erythrocytes as Contrast Agents for Magnetic Resonance Imaging." American Chemical Society, Nano Letters, 6(11);2505-2509.
Doshi et al., 2006, "Red Blood Cell-Mimicking Synthetic Biomaterial Particles," PNAS, 106(51):21495-21499.
Hamidi et al., 2011, "Encapsu of Valproate-Loaded Hydrogel Nanoparticles in Intact Human Erthrocytes: A Novel Nano-Cell Composite for Drug Delivery," Journal of Pharmaceutical Sciences, 100(5):1702-17.
Hu et al., 2012, "Erthrocyte-Inspired Delivery Systems," Adv. Healthcare Mater., 1:537-547.
Markov et al., 2010, Human Erythrocytes as Nonoparticle Carriers for Magnetic Particle Imagining, Physics in Medicine and Biology, 55(21):6461-6473.
Zhang et al. 2010, Transmembrane Delivery of Aggregated [Gd@C82(OH)22]n Nanoparticles Journal of Nanoscience and Nanotechnology, 10(12):8556-8561.
Zhao et al., 2011, "Interaction of Mesoporous Silica Nanoparticles with Human Red Blood Cell Membranes: Size and Surface Effects," ACS Nano, 5(2):1366-1375.
Hu et al., 2011, "Erthrocyte Membrane-Camouflaged Polymeric Nanoparticles as a Biomimetic Delivery Platform," PNAS, 108(27):10980-10985.
Goutayer M, et al. (2010) Tumor targeting of functionalized lipid nanoparticles: assessment by in vivo fluorescence Imaging. Eur J Pharm Biopharm 75:137-147.
Xiao K, et al. (2009) A self-assembling nanoparticle for paclitaxel delivery in ovarian cancer. Biomaterials 30:6006-6016.
Grattan SE, et al. (2007) Nanofabricated particles for engineered drug therapies: a preliminary biodistribution study of PRINT nanoparticles. J Control Release 121:10-18.
Peracchia MT, et al. (1999) Stealth PEGylated polycyanoacrylate nanoparticles for intravenous administration and splenic targeting. J Control Release 60:121-128.
Simberg D, et al. (2007) Biomimetic amplification of nanoparticle homing to tumors. Proc Natl Arad Sci U S A 104:932-936.

Oldenborg PA, et al. (2000) Role of CD47 as a marker of self on red blood cells. Science 288:2051-2054.
Gu F, et al. (2008) Precise engineering of targeted nanoparticles by using self-assembled biointegrated block copolymers. Proc Natl Arad Sci USA 105:2586-2591.
Avgoustakis K, et al. (2003) Effect of copolymer composition on the physicochemical characteristics, in vitro stability, and biodistribution of PLGA-mPEG nanoparticles. Int J Pharm 259:115-127.
Zhang L. (2010) Lipid-polymer hybrid nanoparticles: synthesis, characterization and applications. Nano LIFE 1:163-173.
Sengupta S, et al. (2005) Temporal targeting of tumor cells and neovasculature with a nanoscale delivery system. Nature 436:568-572.
Valencia PM, et al. (2010) Single-step assembly of homogenous lipid-polymeric and lipid-quantum dot nanoparticles anabled by microfluidic rapid mixing. ACS Nano 4:1671-1679.
Liu J, Stace-Naughton A, Jiang X, Brinker CJ (2009) Porous nanoparticle supported lipid bilayers (protocells) as delivery vehicles. J Am Chem Soc 131:1354-1355.
Van Schooneveld MM, et al. (2010) Imaging and quantifying the morphology of an organic-inorganic nanoparticle at the sub-nanometre level. Nat Nanotechnol 5:538-544.
Dodge JT, Mitchell C, Hanahan DJ (1963) The preparation and chemical characteristics of hemoglobin-free ghosts of human erythrocytes. Arch Biochem Biophys 100:119-130.
Zhang L, et al. (2008) Self-assembled lipid-polymer hybrid nanoparticles: A robust drug delivery platform. ACS Nano 2:1696-1702.
Waugh RE, Sarelius IH (1996) Effects of lost surface area on red blood cells and red blood cell survival in mice. Am J Physiol 271:C1847-1852.
Arnold MM, Gorman EM, Schieber LJ, Munson EJ, Berkland C (2007) NanoCipro encapsulation in monodisperse large porous PLGA microparticles. J Control Release 121:100-109.
Jacobs RL, Ailing DW, Cantrell WF (1963) An evaluation of antimalarial combinations against plasmodium berghei in the mouse. J Parasitol 49:920-925.
Lund, R.; Leth-Larsen, R.; Jensen, O. N.; Ditzel, H. J., Efficient isolation and quantitative proteomic analysis of cancer cell plasma membrane proteins for identification of metastasis-associated cell surface markers. J Proteome Res 2009, 8 (6), 3078-3090.
Graham, J. M., Isolation of membranes from tissue culture cells. Methods Mol Biol 1993, 19, 97-108.
Vayro, S.; Kemp, R.; Beechey, R. B.; Shirazi-Beechey, S., Preparation and characterization of basolateral plasma-membrane vesicles from sheep parotid glands. Mechanisms of phosphate and D-glucose transport. Biochem J 1991, 279 ( Pt 3), 843-848.
Navas, P.; Nowack, D. D.; Morre, D. J., Isolation of purified plasma membranes from cultured cells and hepatomas by two-phase partition and preparative free-flow electrophoresis. Cancer Res 1989, 49 (8), 2147-2156.
Henon, M.; Bedouin, A; Polonovski, J., [Isolation, identification and characterization of a plasma membrane preparation of guinea pig macrophages]. C R Acad Sci Hebd Seances Acad Sci D 1977, 285 (1), 121-122.
Boone, C. W.; Ford, L. E.; Bond, H. E.; Stuart, D. C.; Lorenz, D., Isolation of plasma membrane fragments from HeLa cells. J Cell Biol 1969, 41 (2), 378-392.
Petros RA, DeSimone JM. Strategies in the design of nanoparticles for therapeutic applications. Nat. Rev. Drug Discov. 9(8), 615-627 (2010).
Farokhzad OC, Langer R. Impact of Nanotechnology on Drug Delivery. ACS Nano 3(1), 16-20 (2009).
J: Chalmeau, N. Monina, J. Shin, C. Vieu, V. Noireaux, alpha-Hemolysin pore formation into a supported phospholipid bilayer using cell-free expression. Biochim Biophys Acta 1808, 271 (Jan, 2011).
M. Moorjani et al., Nanoerythrosomes, a new derivative of erythrocyte ghost II: identification of the mechanism of action. Anticancer Res 16, 2831 (Sep.-Oct. 1996).
S. Vandana, M. Raje, M. V. Krishnasastry, The role of the amino terminus in the kinetics and assembly of alpha-hemolysin of *Staphylococcus aureus*. J Biol Chem 272, 24858 (Oct. 3, 1997).

(56) References Cited

OTHER PUBLICATIONS

A. Valeva et al., Membrane Insertion of the Heptameric Staphylococcal a—Toxin Pore. J Biol Chem 276, 14835-14841 (May 4, 2001).
Eaton M., "Chemical Modification of Purified Diphtheria Toxin." The Journal of Immunology. 1937 (33): 419-436.
International Search Report and Written Opinion for PCT/US14/67688 dated Nov. 26, 2014 (198 pages).
Aryal, S. et al., "Polymeric Nanoparticles with Precise Ratiometric Control over Drug Loading for Combination Therapy." Mol. Pharmaceutics, 2011, vol. 8, pp. 1401-1407, American Chemical Society.
Tong R, Cheng J. Ring-opening polymerization-mediated controlled formulation of polylactide-drug nanoparticles. J. Am. Chem. Soc. 131(13), 4744-4754 (2009).
Aryal S, Hu CM, Zhang L. Polymer—cisplatin conjugate nanoparticles for acid-responsive drug delivery. ACS Nano 4 (1), 251-258 (2010).
Tong R, Cheng J. Controlled Synthesis of Camptothecin-Polylactide Conjugates and Nanoconjugates. Bioconjug. Chem. 21(1), 111-121 (2010).
Gao W, Chan JM, Farokhzad OC. pH-Responsive Nanoparticles for Drug Delivery. Mol. Pharm. 7(6), 1913-1920 (2010).
Gu F, Zhang L, Teply BA et al. Precise engineering of targeted nanoparticles by using self-assembled biointegrated block copolymers. Proc. Natl. Acad. Sci. USA 105(7), 2586-2591 (2008).
Takae S, Miyata K, Oba M et al. PEG-detachable polyplex micelles based on disulfide-linked block catiomers as bioresponsive nonviral gene vectors. J. Am. Chem. Soc. 130(18), 6001-6009 (2008).
Pompattananangkul D, Zhang L, Olson S et al. Bacterial Toxin-Triggered Drug Release from Gold Nanoparticle-Stabilized Liposomes for the Treatment of Bacterial Infection. J. Am. Chem. Soc. 133(11), 4132-4139 (2011).
Avgoustakis K, Beletsi A, Panagi Z, Klepetsanis P, Karydas AG, Ithakissios DS. PLGA-mPEG nanoparticles of cisplatin: in vitro nanoparticle degradation, in vitro drug release and in Vivo drug residence in blood properties. J. Control. Release 79(1-3), 123-135 (2002).
Li J, Jiang G, Ding F. The effect of pH on the polymer degradation and drug release from PLGA-mPEG microparticles. J. Appl. Polym. Sci. 109(1), 475-482 (2008).
Higuchi T. Rate of release of medicaments from ointment bases containing drugs in suspension. J. Pharm. Sci. 50, 874-875 (1961).
Siepmann J, Peppas NA. Higuchi equation: derivation, applications, use and misuse. Int. J. Pharm. 418(1), 6-12 (2011).
Budhian A, Siegel SJ, Winey KI. Controlling the in vitro release profiles for a system of haloperidol-loaded PLGA nanoparticles. Int. J. Pharm. 346(1-2), 151-159 (2008).
Pitt CG, Schindler A. The kinetics of drug cleavage and release from matrices containing covalent polymer-drug conjugates. J. Control. Release 33(3), 391-395 (1995).
Lowenberg B, Ossenkoppele GJ, van Putten W et al. High-Dose Daunorubicin in Older Patients with Acute Myeloid Leukemia. New Engl. J. Med 361(13), 1235-1248 (2009).
Hu C-MJ, Zhang L Therapeutic Nanoparticles to Combat Cancer Drug Resistance. Curr. Drug Metab. 10(8), 836-841 (2009).
Huwyler J, Cerletti A, Fricker G, Eberle AN, Drewe J. By-passing of P-glycoprotein using immunoliposomes. J. Drug Target. 10(1), 73-79 (2002).
Rapoport N, Marin A, Luo Y, Prestwich GD, Muniruzzaman M. Intracellular uptake and trafficking of pluronic micelles in drug-sensitive and MDR cells: Effect on the intracellular drug localization. J. Pharm. Sci. 91(1), 157-170 (2002).
Blum et al., "Pathways of Antigen Processing," Annu. Rev. Immunol., 2013, 31, pp. 443-473.
Boes et al., "Endosomal processing for antigen presentation mediated by CD1 and Class I major histocompatibility complex: roads to display or destruction," Immunology, 2009, 127(2), pp. 163-170.
Cyrz, Jr. et al., "Effect of Chemical and Heat Inactivation on the Antigenicity and Immunogenicity of Vibrio Cholerae," Infect. Immun., 1982, 38(1), pp. 21-26.

Greenberg et al., "Phase I dose finding studies of an adjuvanted Clostridium difficile toxoid vaccine," Vaccine, 2012, 30, pp. 2245-2249.
Harush-Frenkel et al., "Targeting of nanoparticles to the clathrin-mediated endocytic pathway," Biochem. Biophys. Res. Commun., 2007, 353, pp. 26-32.
Holmgren et al., "Development of improved cholera vaccine based on subunit toxoid," Nature, 1977, 269, pp. 602-604.
Kitchin, N., "Review of diphtheria, tetanus and pertussis vaccines in clinical development," Expert Rev. Vaccines, 2011, 10(5), pp. 605-615.
Metz et al, "Identification of Formaldehyde-induced Modifications in Proteins: Reactions with Model Peptides," J. Biol. Chem., 2004, 279(8), pp. 6235-6243.
Mortimer, E. A. Jr., "Immunization Against Infectious Disease," Science,1978, 200, pp. 902-907.
Parish et al., "Staphylococcal Infection: Antitoxic Immunity," Br. Med. J. 1960, 1(5175), pp. 743-747.
Petrov et al., "Toxicity and Immunogenicity of Neisseria meningitidis Lipopolysaccharide Incorporated into Liposomes," Infect. Immun. 1992, 60(9), pp. 3897-3903.
Schmitt et al., "Bacterial toxins: friends or foes?," Emerg. Infect. Dis., 1999, 5(2), pp. 224-234.
Watts et al., "Pathways of antigen processing and presentation," Rev. Immunogenet. 1999, 1, pp. 60-74.
Zhang et al., "Size-Dependent Endocytosis of Nanoparticles," Adv. Mater., 2009, 21, pp. 419-424.
International Preliminary Report on Patentability for PCT/US2014/067688, dated Jun. 7, 2016.
International Search Report and Written Opinion for PCT/US2014/067688, dated Feb. 4, 2015.
Office Action issued in U.S. Appl. No. 15/100,273, dated Nov. 18, 2016.
Response to Restriction Requirement issued in U.S. Appl. No. 15/100,273, filed Jan. 18, 2017.
Office Action issued in U.S. Appl. No. 15/100,273, dated Feb. 17, 2017.
Taiwanese Office Action for TW Application No. 101119113 dated Jun. 7, 2016 (13 pages with English translation).
Japanese Office Action for JP Application No. 2014-513590 dated Feb. 19, 2016 (9 pages).
Response to Taiwanese Office Action for TW Application No. 101119113 filed on Feb. 5, 2016 (56 pages).
Response to Chinese Office Action for CN Application No. 2012800350485 filed on Jan. 25, 2016 (63 pages).
Taiwanese Office Action for TM Application No. 101119113 dated Oct. 6, 2015 (15 pages).
Ce et al., "Pharmacokinetics of Morphine Loaded into Erythrocyte in Rabbits," Journal of China Pharmaceutical University, 2006, 37(2):150-152.
Sahoo et al., "Enhanced Antiproliferative Activity of Transferrin-Conjugated Paclitaxel-Loaded Nanoparticles is Mediated via Sustained Intracellular Drug Retention, "Molecular Pharmaceutics, 2005, 2(5):373-383.
Response as filed on Nov. 24, 2015 with the European Patent Office in response to the European Supplementary Search Report for EP Application No. 12838792.5 dated May 27, 2015 (9 pages).
Chinese Office Action for CN Application No. 20128003548.5 dated Nov. 10, 2015 (13 pages).
European Search Report for EP Application No. 12838792.5 dated May 7, 2015 (5 pages).
European Supplementary Search Report for EP Application No. 12838792.5 dated May 27, 2015 (4 pages).
Moore et al., "Specific Targeting and Delivery of Virus Envelope-Coated Nanoparticle Cargoes into Receptor-Bearing Cells and Subcellular Compartments," NSTI-Nanotech 2007, vol. 2, pp. 370-373.
Response to Office Action for CN Application No. 2012800350485 filed on Jul. 6, 2015 and English version of remarks and claims.
Moghimi, S. et al., "Long-Circulating and Target-Specific Nanoparticles: Theory to Practice." Pharmacol Rev, vol. 53, No. 2, 2001, pp. 283-318, The American Society for Pharmacology and Experimental Therapeutics.

(56) References Cited

OTHER PUBLICATIONS

Davis M. et al., "Nanoparticle therapeutics: an emerging treatment modality for cancer." Nature Reviews/Drug Discovery, 2008, pp. 71-782, vol. 7, Macmillan Publishers Limited.
Peer, D. et al., "Nanocarriers as an emerging platform for cancer therapy." Nature Nanotechnology, 2007, pp. 751-760, vol. 2, Nature Publishing Group.
Yoo, J. et al., "Factors that Control the Circulation Time of Nanoparticles in Blood: Challenges, Solutions and Future Prospects." Current Pharmaceutical Design, 2010, pp. 2298-2307, vol. 16, Bentham Science Publishers Ltd.
Geng, Y. et al., "Shape effects of filaments versus spherical particles in flow and drug delivery." Nature Nanotechnology, 2007, pp. 249-255, vol. 2, Nature Publishing Group.
Alexis, E et al., "Factors Affecting the Clearance and Biodistribution of Polymeric Nanoparticles." Molecular Pharmaceutics, 2008, pp. 505-515, vol. 5, No. 4.
Knop, K. et al., "Poly(ethylene glycol) in Drug Delivery: Pros and Cons as Well as Potential Alernatives." Angew. Chem. Int. Ed., 2010, pp. 6288-6308, vol. 49, Wiley-VCH Verlag GmbH & Co.
Jiang, S. et al., "Ultralow-Fouling, Functionalizable, and Hydrolyzable Zwitterionic Materials and Their Derivatives for Biological Applications." Adv. Mater., 2010, pp. 920-932, vol. 22, Wiley-VCH Verlag GmbH & Co.
Yang, W. et al., "Functionalizable and ultra stable nanoparticles coated with zwitterionic poly(carboxybetaine) in undiluted blood serum." Biomaterials, 2009, pp. 5617-5621, vol. 30, Elsevier Ltd.
International Search Report and Written Opinion for PCT/US12/039411 dated Aug. 8, 2013 (7 pages).
Tsai RK, Rodriguez PL, Discher DE (2010) Self inhibition of phagocytosis: the affinity of 'marker of self' CD47 for SIRPalpha dictates potency of inhibition but only at low expression levels. Blood Cells Mol Dis 45:67-74.
Merkel TJ, et al. (2011) Using mechanobiological mimicry of red blood cells to extend circulation times of hydrogel microparticles. Proc Natl Acad Sci U S A 108:586-591.
Desilets J, Lejeune A, Mercer J, Gicquaud C (2001) Nanoerythrosomes, a new derivative of erythrocyte ghost: IV. Fate of reinjected nanoerythrosomes. Anticancer Res 21:1741-1747.
Cheng J, et al. (2007) Formulation of functionalized PLGA-PEG nanoparticles for in vivo targeted drug delivery. Biomaterials 28:869-876.
Tanaka M, Sackmann E (2005) Polymer-supported membranes as models of the cell surface. Nature 437:656-663.
Hochmuth RM, Evans CA, Wiles HC, McCown JT (1983) Mechanical measurement of red cell membrane thickness. Science 220:101-102.
Fang RH, Aryal S, Hu CM, Zhang L (2010) Quick synthesis of lipid-polymer hybrid nanoparticles with low polydispersity using a single-step sonication method. Langmuir 26:16958-16962.
Popielarski SR, Pun SH, Davis ME (2005) A nanoparticle-based model delivery system to guide the rational design of gene delivery to the liver. 1. Synthesis and characteriza.

\* cited by examiner

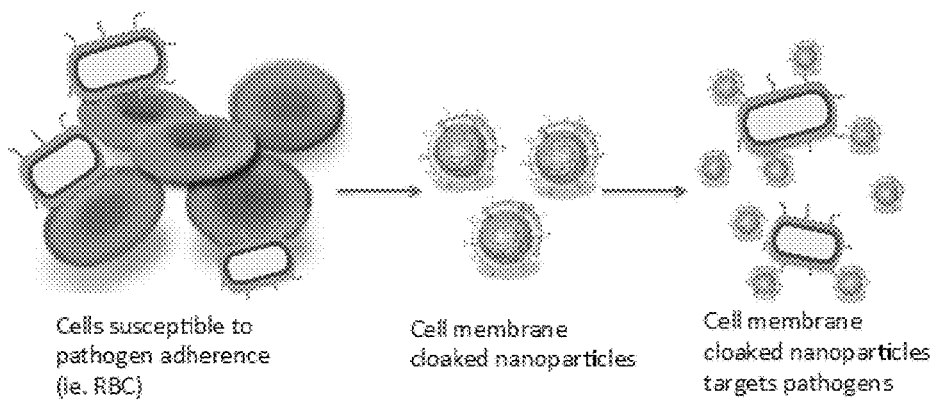
FIG. 2
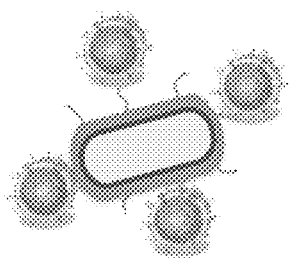
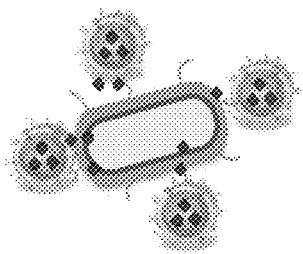
FIG. 3A　　　　　　　　　　FIG. 3B
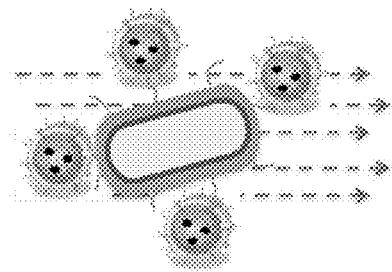
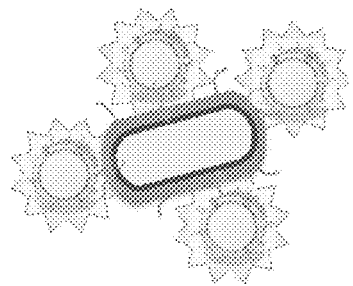
FIG. 3C　　　　　　　　　　FIG. 3D

NANOPARTICLES LEVERAGE BIOLOGICAL MEMBRANES TO TARGET PATHOGENS FOR DISEASE TREATMENT AND DIAGNOSIS

CROSS-REFERENCE TO RELATED APPLICATIONS

This application is a continuation of PCT Application No. PCT/US2014/050355 filed Aug. 8, 2014 which claims priority to U.S. Provisional Application Ser. No. 61/863,528, filed Aug. 8, 2013, entitled "Nanoparticles Leverage Biological Membranes to Target Pathogens for Disease Treatment and Diagnosis", the entire contents of which are incorporated by reference herein.

STATEMENT REGARDING FEDERALLY SPONSORED RESEARCH

This invention was made with Government support under Grant No. DK 095168 awarded by the National Institutes of Health. The Government has certain rights in the invention.

FIELD OF THE INVENTION

The present invention relates to methods and pharmaceutical compositions for treating or preventing an infection in a subject using a nanoparticle comprising an inner core comprising a non-cellular material, and an outer surface comprising a cellular membrane configured for adhesion of a pathogen that causes said infection.

SUMMARY OF THE INVENTION

In one aspect, the present invention provides for a method for treating or preventing an infection in a subject, which method comprises administering, to a subject in need of treatment or prevention of an infection, or to cells of said subject, an effective amount of a nanoparticle comprising a) an inner core comprising a non-cellular material, and b) an outer surface comprising a cellular membrane configured for adhesion of a pathogen that causes said infection. Exemplary infection includes infection caused by a virus, bacterium, fungus, or protozoan.

In another aspect, the present invention is directed to use of an effective amount of a nanoparticle for the manufacture of a medicament for treating or preventing an infection in a subject, wherein said nanoparticle comprises: a) an inner core comprising a non-cellular material, and b) an outer surface comprising a cellular membrane adapted for adhesion of a pathogen that causes said infection.

In still another aspect, the present invention provides for a combination of prophylactics or therapeutic agents for treating and/or preventing an infection in a subject, which combination comprises an effective amount of a nanoparticle and an effective amount of a second prophylactic or therapeutic agent for treating and/or preventing an infection in a subject, wherein said nanoparticle comprises: a) an inner core comprising a non-cellular material, and b) an outer surface comprising a cellular membrane adapted for adhesion of a pathogen that causes said infection. The present invention also provides for a pharmaceutical composition comprising the combination and a method for treating and/or preventing an infection in a subject using the combination or the pharmaceutical composition comprising the combination.

In some aspects, the prevent disclosure relates to U.S. application Ser. No. 13/827,906, filed Mar. 14, 2013, International Application No. PCT/US2012/039411, filed May 24, 2012 and published as WO 2013/052167 and U.S. provisional application Ser. No. 61/492,626, filed Jun. 2, 2011. The contents of the above applications are incorporated herein by reference in their entireties.

BRIEF DESCRIPTION OF THE DRAWINGS

FIG. 1A. Pseudo-color SEM image of influenza viruses (white) adhering to RBCs (red greyscales) (Source: NIBSC/SCIENCE PHOTO LIBRARY). FIG. 1B. Fluorescence image of enteropathogenic E. coli (blue greyscales) adhesion to RBCs (red greyscales)[20]. FIG. 1C. Transmission electron micrograph of P. falciparum binding to RBCs[21]. FIG. 1D. Microscopy of C. albicans adhesion to RBCs[22].

FIG. 2. Schematics of nanoparticles that leverage cellular membranes for pathogen targeting.

FIGS. 3A-3D. Applications of cell-membrane coated nanoparticles that target pathogenic bodies. FIG. 3A. The nanoparticles can encase pathogenic bodies and interfere with their adhesion mechanisms that are crucial for disease pathogenesis. FIG. 3B. Cell-membrane coated nanoparticles carrying antibiotics can target pathogenic bodies for effective drug delivery. FIG. 3C. Cell-membrane coated nanoparticles carrying magnetic materials (e.g., iron oxide nanoparticles) can be used to isolate and remove pathogens with an external magnetic field. FIG. 3D. Cell-membrane coated nanoparticles with optical properties (e.g. gold nanoparticles) can be used for pathogen detection.

DETAILED DESCRIPTION OF THE INVENTION

Figure 1A:
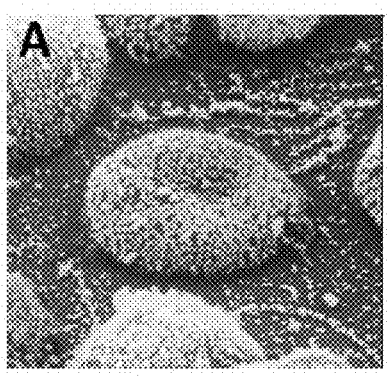
FIGS. 1A-1D. Examples of pathogen adhesion to cellular membranes.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, Molecular Cloning: A Laboratory Manual, 2$^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); and Remington, The Science and Practice of Pharmacy, 20$^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

Viral membrane: As used herein, the term "membrane derived from a virus" refers to viral envelopes that cover the nucleic acid or protein capsids of a virus, and typically contain cellular membrane proteins derived from portions of the host cell membrane (phospholipid and proteins) and include some viral glycoproteins. The viral envelop fuses with the host's membrane, allowing the capside and viral genome to enter and infect the host.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibiotics, antibodies and aptamers can be added to the outer surface of the membrane to enhance site targeting, such as to cell surface epitopes found in cancer cells. The membrane of the nanoparticles can also comprise particles that can be biodegradable, magnetic (e.g., iron oxide), and cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

Vaccine: a composition capable of eliciting in a patient a beneficial active or passive immune response to a specific antigen. While protective immunity may be desired, it is understood that various levels of temporal immune response can be beneficial.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be constituted as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Treating or Preventing an Infection in a Subject

In one aspect, the present invention provides for a method for treating or preventing an infection in a subject, which method comprises administering, to a subject in need of treatment or prevention of an infection, or to cells of said subject, an effective amount of a nanoparticle comprising a) an inner core comprising a non-cellular material, and b) an outer surface comprising a cellular membrane configured for adhesion of a pathogen that causes said infection.

The present methods can be used to treat or prevent an infection in any suitable subject. In some embodiments, the subject is a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present methods can be used for treating an infection in a subject. In other embodiments, the present methods can be used for preventing an infection in a subject.

The present methods can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. In some embodiments, the inner core can comprise a polymeric particle core. In some embodiments, the polymeric particle core can comprise an optical shift property. In other embodiments, the polymeric particle core can comprise metal, e.g., gold, iron oxide or a quantum dot.

The nanoparticle can comprise a cellular membrane derived from any suitable cell that is a target or that binds to a pathogen. The nanoparticle can also comprise any suitable cellular membrane derived from a cell that is a target or that binds to a pathogen. For example, the nanoparticle can comprise a plasma membrane or an intracellular membrane derived from a cell that is a target or that binds to a pathogen. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, a lymphocyte or a platelet, e.g., a plasma membrane derived from a human red blood cell, lymphocyte or platelet. In some embodiments, the nanoparticle can comprise any suitable naturally occurring cellular membrane derived from a red blood cell, a lymphocyte or a platelet. In some embodiments, the cellular membrane comprises a naturally occurring plasma membrane derived from a red blood cell, a lymphocyte or a platelet, e.g., a naturally occurring plasma membrane derived from a human red blood cell, lymphocyte or platelet.

The present methods can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle.

The nanoparticle can comprise any suitable types of releasable cargo. For example, the releasable cargo can be a therapeutic agent, a prophylactic agent, a diagnostic or marker agent, a prognostic agent, an isolation agent, a monitoring agent, or a combination thereof. In another example, the releasable cargo can be a metallic particle, a polymeric particle, a dendrimer particle, or an inorganic particle. In some embodiments, the therapeutic agent or prophylactic agent can be an anti-viral agent, an antibiotic, an anti-fungal agent, or an anti-protozoa agent. For example, the therapeutic agent or prophylactic agent can be quinine. In other embodiments, the isolation agent can be a magnetic material, e.g., a magnetic material comprises iron oxide, to facilitate isolation and removal of a pathogen from the subject.

The nanoparticle can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell, e.g., red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., the red blood cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the pathogen's target cell, e.g., red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the pathogen's target cell, e.g., red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the subject, e.g., a mammal. For example, the cellular membrane can be derived from a cell, e.g., a red blood cell, from the same species of the mammal. In another example, the mammal is a human and the cellular membrane is derived from a human cell, e.g., a human red blood cell. In some embodiments, the cellular membrane can be derived from a cell, e.g., a red blood cell, of the mammal to be treated. For example, the cellular membrane can be derived from a red blood cell of the human to be treated.

The present methods can be used for treating or preventing any suitable infection in a subject. For example, the cellular membrane of the nanoparticle can be adapted for adhesion of a virus, bacterium, fungus, or protozoan, and the present methods can be used to treat or prevent an infection of a virus, bacterium, fungus or protozoa in the subject. In some embodiments, the present methods can be used to treat or prevent an infection of a virus, e.g., an influenza virus or a human immunodeficiency virus. In other embodiments, the present methods can be used to treat or prevent an infection of a bacterium, e.g., *E. coli* or *Staphylococcus aureus*. In other embodiments, the present methods can be used to treat or prevent an infection of a fungus, e.g., *Candida albicans*. For example, the present methods can be used to treat or prevent opportunistic, oral or genital infection of *Candida albicans*, or candidal onychomycosis in a subject. In another example, the present methods can be used to treat or prevent infection of *Candida albicans* in an immunocompromised subject, or a subject that receives an implantable medical device. The exemplary immunocompromised subjects include an AIDS patient, a cancer chemotherapy patient, or an organ or bone marrow transplantation recipient.

In some embodiments, the present methods can be used to treat or prevent an infection of a protozoan, e.g., a parasitic protozoan that causes malaria in a subject. For example, the parasitic protozoan can be a parasitic protozoan that causes malaria in a subject, e.g., a human, and the present methods can be used to treat or prevent malaria in the subject or human. The exemplary protozoa include *P. falciparum, P. malariae, P. ovale, P. vivax* and *P. knowlesi*. In another example, the present methods can be used to treat or prevent severe malaria, uncomplicated malaria or cerebral malaria.

In some embodiments, the present methods can be used to intervene in an adhering mechanism of a pathogen and comprise: a) administering the nanoparticle to the subject under pathogenic assault or cells of the subject; b) enclosing the pathogen in a layer of the nanoparticle; c) precluding the enclosed pathogen from interaction with the subject or cells of the subject; and d) intervening the pathogen proliferative cycle in the subject or cells of the subject.

In other embodiments, the present methods can be used to facilitate isolation and removal of a pathogen from systemic infections and comprise: a) administering the nanoparticle to the subject under pathogenic assault or cells of the subject; b) adhering the nanoparticle to a systemic pathogen; and c) isolating and removing the pathogen. In one example, the nanoparticle can encapsulate a magnetic material, e.g., iron oxide, in the polymeric particle core and coated with red blood cell membrane. In another example, a magnetic field can be applied in a dialysis device to isolate and remove the pathogen. The present methods can be used to facilitate isolation and removal of any suitable pathogen, e.g., influenza virus, *E. coli, P. falciparum, C. albicans*, and other bacteria or fungus.

In still some embodiments, the present method is used to monitor and/or diagnose pathogen targeting and comprises: a) administering the nanoparticle to the subject under pathogenic assault or cells of the subject, wherein the polymeric particle core of the nanoparticle comprises an optical shift property; b) attaching the nanoparticle to a pathogen body, and c) monitoring and evaluating an optical shift in the pathogen body attached to the nanoparticle.

In some embodiments, the present methods can further comprise administering another active ingredient to the mammal. The other active ingredient can be used to treat or prevent the infection in the subject.

In some embodiments, the present methods can further comprise administering a pharmaceutically acceptable carrier or excipient to the subject.

The nanoparticle can be administered using any suitable delivery mechanisms or techniques. In some embodiments, the nanoparticle can be administered alone. In other embodiments, the nanoparticle can be administered with a pharmaceutically acceptable carrier or excipient. In still other embodiments, the nanoparticle can be administered via a medicament delivery system.

In some embodiments, the present methods can further comprise assessing efficacy of the nanoparticle and/or the other active ingredient in treating or preventing the infection in the subject. In some embodiments, the efficacy of nanoparticle can be assessed by one or more tests, e.g., 2, 3, 4, 5, 6, 7, 8 or 9 tests.

The nanoparticle, alone or in combination with other active ingredient(s), can be administered via any suitable administration routes. In some embodiments, the nanoparticle, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

C. Use of an Effective Amount of a Nanoparticle for the Manufacture of a Medicament for Treating or Preventing an Infection in a Subject In another aspect, the present invention is directed to an effective amount of a nanoparticle for the manufacture of a medicament for treating or preventing an infection in a subject, wherein said nanoparticle comprises: a) an inner core comprising a non-cellular material, and b) an outer surface comprising a cellular membrane adapted for adhesion of a pathogen that causes said infection.

The present manufactured medicament can be used to treat or prevent an infection in any suitable subject, e.g., a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present manufactured medicament can be used for treating an infection in a subject. In other embodiments, the present manufactured medicament can be used for preventing an infection in a subject.

The manufactured medicament can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. In some embodiments, the inner core can comprise a polymeric particle core. In some embodiments, the polymeric particle core can comprise an optical shift property. In other embodiments, the polymeric particle core can comprise metal, e.g., gold, iron oxide or a quantum dot.

The nanoparticle can comprise a cellular membrane derived from any suitable cell that is a target or that binds to a pathogen. The nanoparticle can also comprise any suitable cellular membrane derived from a cell that is a target or that binds to a pathogen. For example, the nanoparticle can comprise a plasma membrane or an intracellular membrane derived from a red blood cell. In some embodiments, the cellular membrane comprises a plasma membrane derived from a red blood cell, a lymphocyte or a platelet, e.g., a plasma membrane derived from a human red blood cell, lymphocyte or platelet. In some embodiments, the nanoparticle can comprise any suitable naturally occurring cellular membrane derived from a red blood cell, a lymphocyte or a platelet. In some embodiments, the cellular membrane comprises a naturally occurring plasma membrane derived from a red blood cell, a lymphocyte or a platelet, e.g., a naturally occurring plasma membrane derived from a human red blood cell, lymphocyte or platelet.

The manufactured medicament can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle.

The nanoparticle can comprise any suitable types of releasable cargo. For example, the releasable cargo can be a therapeutic agent, a prophylactic agent, a diagnostic or marker agent, a prognostic agent, an isolation agent, a monitoring agent, or a combination thereof. In another example, the releasable cargo can be a metallic particle, a polymeric particle, a dendrimer particle, or an inorganic particle. In some embodiments, the therapeutic agent or prophylactic agent can be an anti-viral agent, an antibiotic, an anti-fungal agent, or an anti-protozoa agent. For example, the therapeutic agent or prophylactic agent can be quinine. In other embodiments, the isolation agent can be a magnetic material, e.g., a magnetic material comprises iron oxide, to facilitate isolation and removal of a pathogen from the subject.

The nanoparticle can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell, e.g., red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., the red blood cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the pathogen's target cell, e.g., red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the pathogen's target cell, e.g., red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the subject, e.g., a mammal. For example, the cellular membrane can be derived from a cell, e.g., a red blood cell, from the same species of the mammal. In another example, the mammal is a human and the cellular membrane is derived from a human cell, e.g., a human red blood cell. In some embodiments, the cellular membrane can be derived from a cell, e.g., a red blood cell, of the mammal to be treated. For example, the cellular membrane can be derived from a red blood cell of the human to be treated.

The present manufactured medicament can be used to treat or prevent any suitable infection in a subject. For example, the cellular membrane of the nanoparticle can be adapted for adhesion of a virus, bacterium, fungus, or protozoan, and the present methods can be used to treat or prevent an infection of a virus, bacterium, fungus or protozoa in the subject. In some embodiments, the present manufactured medicament can be used to treat or prevent an infection of a virus, e.g., an influenza virus or a human immunodeficiency virus. In other embodiments, the present manufactured medicament can be used to treat or prevent an infection of a bacterium, e.g., *E. coli* or *Staphylococcus aureus*. In still other embodiments, the present manufactured medicament can be used to treat or prevent an infection of a fungus, e.g., *Candida albicans*. For example, the present manufactured medicament can be used to treat or prevent opportunistic, oral or genital infection of *Candida albicans*, or candidal onychomycosis in a subject. In another example, the present manufactured medicament can be used to treat or prevent infection of *Candida albicans* in an immunocompromised subject, or a subject that receives an implantable medical device. The exemplary immunocompromised subjects include an AIDS patient, a cancer chemotherapy patient, or an organ or bone marrow transplantation recipient.

In some embodiments, the present manufactured medicament can be used to treat or prevent an infection of a protozoan, e.g., a parasitic protozoan that causes malaria in a subject. For example, the parasitic protozoan can be a parasitic protozoan that causes malaria in a subject, e.g., a human, and the present methods can be used to treat or prevent malaria in the subject or human. The exemplary protozoa include *P. falciparum, P. malariae, P. ovale, P. vivax* and *P. knowlesi*. In another example, the present manufactured medicament can be used to treat or prevent severe malaria, uncomplicated malaria or cerebral malaria.

In some embodiments, the present manufactured medicament can be used to intervene in an adhering mechanism of a pathogen and comprise: a) administering the nanoparticle to the subject under pathogenic assault or cells of the subject; b) enclosing the pathogen in a layer of the nanoparticle; c) precluding the enclosed pathogen from interaction with the subject or cells of the subject; and d) intervening the pathogen proliferative cycle in the subject or cells of the subject.

In other embodiments, the present manufactured medicament can be used to facilitate isolation and removal of a pathogen from systemic infections and comprise: a) administering the nanoparticle to the subject under pathogenic assault or cells of the subject; b) adhering the nanoparticle to a systemic pathogen; and c) isolating and removing the pathogen. In one example, the nanoparticle can encapsulate a magnetic material, e.g., iron oxide, in the polymeric particle core and coated with red blood cell membrane. In another example, a magnetic field can be applied in a dialysis device to isolate and remove the pathogen. The present manufactured medicament can be used to facilitate isolation and removal of any suitable pathogen, e.g., influenza virus, *E. coli, P. falciparum, C. albicans*, and other bacteria or fungus.

In still some embodiments, the present manufactured medicament can be used to monitor and/or diagnose pathogen targeting and comprises: a) administering the nanoparticle to the subject under pathogenic assault or cells of the subject, wherein the polymeric particle core of the nanoparticle comprises an optical shift property; b) attaching the nanoparticle to a pathogen body, and c) monitoring and evaluating an optical shift in the pathogen body attached to the nanoparticle.

In some embodiments, the present manufactured medicament can further comprise another active ingredient to the mammal. The other active ingredient can be used to treat, prevent the infection in the subject.

In some embodiments, the present manufactured medicament can further comprise a pharmaceutically acceptable carrier or excipient to the mammal.

The manufactured medicament can be administered using any suitable delivery mechanisms or techniques. In some embodiments, the nanoparticle in the manufactured medicament can be administered alone. In other embodiments, the nanoparticle in the manufactured medicament can be administered with a pharmaceutically acceptable carrier or excipient. In still other embodiments, the nanoparticle in the manufactured medicament can be administered via a medicament delivery system.

The manufactured medicament, alone or in combination with other active ingredient(s), can be administered via any suitable administration routes. In some embodiments, the manufactured medicament, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

D. Combinations for Treating and/or Preventing an Infection in a Subject and Uses Thereof In still another aspect, the present invention provides for a combination for treating and/or preventing an infection in a subject, which combination comprises an effective amount of a nanoparticle and an effective amount of a second prophylactic or therapeutic agent for treating and/or preventing an infection in a subject, wherein said nanoparticle comprises: a) an inner core comprising a non-cellular material, and b) an outer surface comprising a cellular membrane adapted for adhesion of a pathogen that causes said infection.

The present combination can be made, stored and/or used in any suitable formulation. In some embodiments, the present invention provides for a pharmaceutical composition comprising the above combination admixed with at least one pharmaceutically acceptable carrier or excipient. In other embodiments, the present invention provides for a method for treating or preventing an infection in a subject, which method comprises administering, to a subject in need of treatment or prevention of an infection, or to cells of said subject, an effective amount of the above combination or a pharmaceutical composition.

The above combination or pharmaceutical composition can be used to treat or prevent an infection in any suitable subject, e.g., a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the above combination or pharmaceutical composition can be used for treating an infection in a subject. In other embodiments, the above combination or pharmaceutical composition can be used for preventing an infection in a subject.

The above combination or pharmaceutical composition can comprise any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. In some embodiments, the inner core can comprise a polymeric particle core. In some embodiments, the polymeric particle core can comprise an optical shift property. In other embodiments, the polymeric particle core can comprise metal, e.g., gold, iron oxide or a quantum dot.

The nanoparticle can comprise a cellular membrane derived from any suitable cell that is a target or that binds to a pathogen. The nanoparticle can also comprise any suitable cellular membrane derived from a cell that is a target or that binds to a pathogen. For example, the nanoparticle can comprise a plasma membrane or an intracellular membrane derived from a red blood cell. In some embodiments, the cellular membrane comprises a plasma membrane derived from a red blood cell, a lymphocyte or a platelet, e.g., a plasma membrane derived from a human red blood cell, lymphocyte or platelet. In some embodiments, the nanoparticle can comprise any suitable naturally occurring cellular membrane derived from a red blood cell, a lymphocyte or a platelet. In some embodiments, the cellular membrane comprises a naturally occurring plasma membrane derived from a red blood cell, a lymphocyte or a platelet, e.g., a naturally occurring plasma membrane derived from a human red blood cell, lymphocyte or platelet.

The above combination or pharmaceutical composition can comprise a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle.

The nanoparticle can comprise any suitable types of releasable cargo. For example, the releasable cargo can be a therapeutic agent, a prophylactic agent, a diagnostic or marker agent, a prognostic agent, an isolation agent, a monitoring agent, or a combination thereof. In another example, the releasable cargo can be a metallic particle, a polymeric particle, a dendrimer particle, or an inorganic particle. In some embodiments, the therapeutic agent or prophylactic agent can be an anti-viral agent, an antibiotic, an anti-fungal agent, or an anti-protozoa agent. For example, the therapeutic agent or prophylactic agent can be quinine. In other embodiments, the isolation agent can be a magnetic material, e.g., a magnetic material comprises iron oxide, to facilitate isolation and removal of a pathogen from the subject.

The nanoparticle can have any suitable size. For example, the nanoparticle can have a diameter from about 10 nm to about 10 µm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell, e.g., red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., the red blood cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the pathogen's target cell, e.g., red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the pathogen's target cell, e.g., red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the subject, e.g., a mammal. For example, the cellular membrane can be derived from a cell, e.g., a red blood cell, from the same species of the mammal. In another example, the mammal is a human and the cellular membrane is derived from a human cell, e.g., a human red blood cell. In some embodiments, the cellular membrane can be derived from a cell, e.g., a red blood cell, of the mammal to be treated. For example, the cellular membrane can be derived from a red blood cell of the human to be treated.

The present combination or pharmaceutical composition can be used to treat or prevent any suitable infection in a subject. For example, the cellular membrane of the nanoparticle can be adapted for adhesion of a virus, bacterium, fungus, or protozoan, and the present combination or pharmaceutical composition can be used to treat or prevent an infection of a virus, bacterium, fungus or protozoa in the subject. In some embodiments, the present combination or pharmaceutical composition can be used to treat or prevent an infection of a virus, e.g., an influenza virus or a human immunodeficiency virus. In other embodiments, the present combination or pharmaceutical composition can be used to treat or prevent an infection of a bacterium, e.g., *E. coli* or *Staphylococcus aureus*. In still other embodiments, the present combination or pharmaceutical composition can be used to treat or prevent an infection of a fungus, e.g., *Candida albicans*. For example, the present combination or pharmaceutical composition can be used to treat or prevent opportunistic, oral or genital infection of *Candida albicans*, or candidal onychomycosis in a subject. In another example, the present combination or pharmaceutical composition can be used to treat or prevent infection of *Candida albicans* in an immunocompromised subject, or a subject that receives an implantable medical device. The exemplary immunocompromised subjects include an AIDS patient, a cancer chemotherapy patient, or an organ or bone marrow transplantation recipient.

In some embodiments, the present combination or pharmaceutical composition can be used to treat or prevent an infection of a protozoan, e.g., a parasitic protozoan that causes malaria in a subject. For example, the parasitic protozoan can be a parasitic protozoan that causes malaria in a subject, e.g., a human, and the present combination or pharmaceutical composition can be used to treat or prevent malaria in the subject or human. The exemplary protozoa include *P. falciparum, P. malariae, P. ovale, P. vivax* and *P. knowlesi*. In another example, the present combination or pharmaceutical composition can be used to treat or prevent severe malaria, uncomplicated malaria or cerebral malaria.

In some embodiments, the present combination or pharmaceutical composition can be used to intervene in an adhering mechanism of a pathogen and comprise: a) administering the combination comprising nanoparticle to the subject under pathogenic assault or cells of the subject; b) enclosing the pathogen in a layer of the nanoparticle; c) precluding the enclosed pathogen from interaction with the subject or cells of the subject; and d) intervening the pathogen proliferative cycle in the subject or cells of the subject.

In other embodiments, the present combination or pharmaceutical composition can be used to facilitate isolation and removal of a pathogen from systemic infections and comprise: a) administering the combination comprising the nanoparticle to the subject under pathogenic assault or cells of the subject; b) adhering the nanoparticle to a systemic pathogen; and c) isolating and removing the pathogen. In one example, the nanoparticle can encapsulate a magnetic material, e.g., iron oxide, in the polymeric particle core and coated with red blood cell membrane. In another example, a magnetic field can be applied in a dialysis device to isolate and remove the pathogen. The present combination or pharmaceutical composition can be used to facilitate isolation and removal of any suitable pathogen, e.g., influenza virus, *E. coli, P. falciparum, C. albicans*, and other bacteria or fungus.

In still some embodiments, the present combination or pharmaceutical composition can be used to monitor and/or diagnose pathogen targeting and comprises: a) administering the combination comprising the nanoparticle to the subject under pathogenic assault or cells of the subject, wherein the polymeric particle core of the nanoparticle comprises an optical shift property; b) attaching the nanoparticle to a pathogen body, and c) monitoring and evaluating an optical shift in the pathogen body attached to the nanoparticle.

In some embodiments, the present combination or pharmaceutical composition can further comprise a pharmaceutically acceptable carrier or excipient to the mammal.

The present combination or pharmaceutical composition can be administered using any suitable delivery mechanisms or techniques. In some embodiments, the nanoparticle in the present combination or pharmaceutical composition can be administered alone. In other embodiments, the nanoparticle in the present combination or pharmaceutical composition can be administered with a pharmaceutically acceptable carrier or excipient. In still other embodiments, the nanoparticle in the present combination or pharmaceutical composition can be administered via a medicament delivery system.

The present combination or pharmaceutical composition can be administered via any suitable administration routes. In some embodiments, the present combination or pharmaceutical composition can be administered via oral, parenteral, rectal, nasal, topical, or ocular routes, or by inhalation. Exemplary parenteral administration routes include intravenous, intramuscular, intraperitoneal, intranasal, and subcutaneous routes.

E. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, antioxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

F. Exemplary Embodiments

Figure 1B:
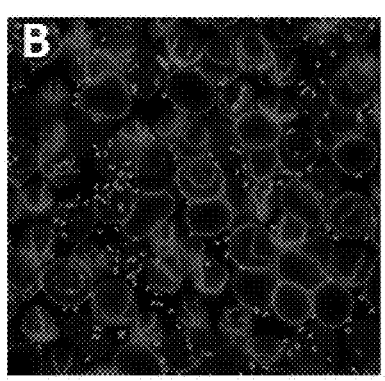
Figure 1C:
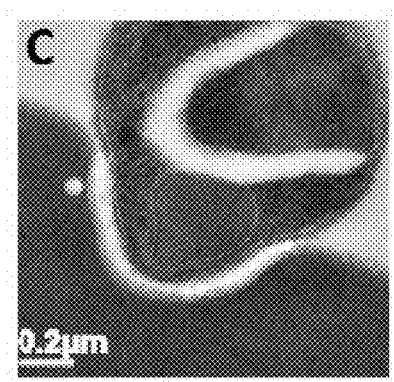
Figure 1D:
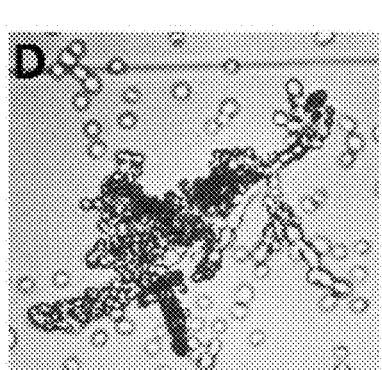

Many pathogens, including viruses, bacteria, parasites, and fungi possess surface proteins or molecules with high affinities to cellular membranes (FIGS. 1A-1D). Such cell-specific membrane adhesive properties allow the pathogen to target particular cell types and in turn facilitate host invasion, nutrient derivation, and immune evasion[1-4]. Examples of pathogen/cell membrane adhesions include but are not limited to the following Table 1.

TABLE 1

Examples of pathogen/cell membrane adhesions

|  | Pathogen | Cell type | Ref |
|---|---|---|---|
| Virus | Influenza virus | Red blood cell | 5-7 |
|  | Human immunodeficiency virus | T-lymphocytes | 8-10 |
| Bacteria | *Escherichia coli* | Red blood cell | 11, 12 |
|  | *Staphylococcus aureus* | platelets | 13, 14 |
| Parasites | *Plasmodium falciparum* | Red blood cell | 15-17 |
| Fungi | *Candida albicans* | Red blood cell | 18 |

Membrane-bound surface proteins and glycans on cells are among the moieties that pathogens exploit for the pathogen/cell adhesion. For instance, influenza viruses possess hemagglutinins, which attach to the surface sialic acid on red blood cells (RBCs)[5]. *P. falciparum*, the parasite responsible for malaria, are equipped with erythrocyte binding antigens (EBA-175, EBA-140, and EBA-181) that target glycophorins on RBCs[15]. Mannan, a polysaccharide on *C. albicans* has also been found to bind to band 3 protein of human RBCs[18]. These pathogen/cell membrane interactions provide an opportunity for pathogen targeting via effective leveraging of cellular membranes.

Translocating a cell membrane onto nanoparticle surfaces enables nanoparticle functionalization with membrane surface moieties to which many pathogens have affinity. RBC membrane cloaked nanoparticles (RBC-NPs), for instance, have been prepared and they possess the membrane proteins and glycans found on RBCs[19]. By leveraging the cell membrane materials and properties, these nanoparticles can mimic source cells in their adhesive properties to pathogens and thereby enable targeted delivery to pathogenic bodies such as influenza viruses and *P. falciparum* (FIG. 2). Unique treatment options can be developed using these cell membrane coated nanoparticles with different modalities encapsulated inside the particle cores. Applications of these nanoparticles toward pathogen treatments include but are not limited to intervening adhering mechanism of pathogens, enabling targeted antibiotics delivery, facilitating pathogen removal, and permitting disease diagnosis (FIG. 3A-3D).

Generally, membrane encapsulated nanoparticles, such as are described in the art, can be found for example in PCT/US2012/039411, which is incorporated by reference herein.

In some embodiments, the present invention provides a medicament delivery system, and/or a pharmaceutical composition comprising the inventive nanoparticle. In certain embodiments, the medicament delivery system and/or the pharmaceutical composition of the present invention further comprises one or more additional active ingredient and/or a medically or pharmaceutically acceptable carrier or excipient that can be administered along with or in combination with the nanoparticle of the present invention.

In some embodiments, the present invention further provides a method for treating and/or preventing a disease or condition in a subject in need using the inventive nanoparticles, the medicament delivery system, or the pharmaceutical composition comprising the same. In certain embodiments, the cellular membrane of the nanoparticle used for the inventive method is derived from a cell of the same species of the subject or is derived from a cell of the subject. In certain embodiments, the cellular membrane of the nanoparticle used for the inventive method is derived from a red blood cell of the same species of the subject and the red blood cell has the same blood type of the subject. In certain embodiments, the nanoparticle, the medicament delivery system, or the pharmaceutical composition is administered via any suitable administration route. For example, the nanoparticle, the medicament delivery system, or the pharmaceutical composition can be administered via an oral, nasal, inhalational, parental, intravenous, intraperitoneal, subcutaneous, intramuscular, intradermal, topical, or rectal route.

In other embodiments, the nanoparticle is administered via a medicament delivery system. In yet other embodiments, the inventive method further comprises administering another active ingredient, or a pharmaceutically acceptable carrier or excipient, to the subject in need. The inventive method further provides that the nanoparticle of the present invention can be administered systemically or to a target site of the subject in need. Use of an effective amount of nanoparticles of the present invention for the manufacture of a medicament for treating or preventing a disease or condition in a subject in need is also provided.

In some embodiments, the present invention contemplates treatments, prevention, diagnosis and/or prognosis of any diseases, disorders, or physiological or pathological conditions, including, but not limited to, an infectious disease, a parasitic disease, a neoplasm, a disease of the blood and blood-forming organs, a disorder involving the immune mechanism, endocrine, nutritional and metabolic diseases, a mental and behavioral disorder, a disease of the nervous system, a disease of the eye and adnexa, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

Other objects, advantages and features of the present invention will become apparent from the following specification taken in conjunction with the accompanying drawings.

In certain embodiments, the present invention provides novel nanoparticles, method of using and making thereof. More specifically, the inventive nanoparticle comprises a) an inner core comprising a non-cellular material; and b) an outer surface comprising a membrane derived from a cell or a membrane derived from a virus.

In certain embodiments, the inner core of the inventive nanoparticle supports the outer surface and can be of any shape, including but not limited to, sphere, square, rectangle, triangle, circular disc, cube-like shape, cube, rectangular parallelepiped (cuboid), cone, cylinder, prism, pyramid, right-angled circular cylinder, and other regular or irregular shape. In other embodiments, the non-cellular material of the inner core comprises a biocompatible synthetic material, including but not limited to, poly(lactic-co-glycolic acid), polylactic acid, polyglycolic acid, polycaprolactone, polylysine, polyglutamic acid, and any other suitable synthetic material or the like.

In certain embodiments, the membrane of the outer surface of the invention nanoparticle comprises naturally occurring cellular membrane derived from plasma membrane of a cell from any unicellular (e.g. a bacterium or fungus) or multicellular organisms (e.g., a plant, an animal, a non-human mammal, or a human). The naturally occurring cellular plasma membrane maintains natural structural integrity and activity of the membrane. For instance, the lipid bilayer structure and at least some of the associated membrane proteins embedded therewith are intact, such that the membrane encapsulation substantially lacks immunogenicity to a species or subject from which the membrane is derived.

In certain embodiments, the cell includes, but is not limited to, a blood cell such as a red blood cell (RBC), a white blood cell (WBC), and a platelet, an immune cell, such as a macrophage, a monocyte, a B-cell, and a T-cell, a tumor or cancer cell, and other cells, such as an epithelial cell, an endothelial cell, and a neural cell. In other embodiments, the membrane of the outer surface is derived from non-terminally differentiated or pluripotent stem cells, such as a hematopoietic stem cell, a bone marrow stem cell, a mesenchymal stem cell, a cardiac stem cell, or a neural stem cell.

In yet other embodiments, the cellular membrane is derived from a cell component including, but not limited to, an exosome, a secretory vesicle or a synaptic vesicle. In certain embodiments, the outer surface of the nanoparticle of the present invention further comprises a synthetic membrane or synthetic components, along with the naturally derived membrane.

The membranes according to the invention can be obtained and assembled by methods described herein and known in the art, for example, see e.g., WO 2013/052167, Desilets et al., *Anticancer Res.* 21: 1741-47; Lund et al., *J Proteome Res* 2009, 8 (6), 3078-3090; Graham, *Methods Mol Biol* 1993, 19, 97-108; Vayro et al., *Biochem J* 1991, 279 (Pt 3), 843-848; Navas et al., *Cancer Res* 1989, 49 (8), 2147-2156; Henon et al., *C R Acad Sci Hebd Seances Acad Sci D* 1977, 285 (1), 121-122; and Boone et al., *J Cell Biol* 1969, 41 (2), 378-392), the entire contents of which are incorporated by reference herewith.

Intervening Adhering Mechanism of Pathogens:

Cell-membrane coated nanoparticles can preoccupy membrane-adhering molecules on pathogens, thereby interfering with the adhesion mechanism that aids disease pathogenesis. Administration of cell-membrane coated nanoparticles in copious amount can enclose pathogens in a layer of nanoparticles, thereby precluding their interaction with host cells and offering the opportunity to intervene their proliferative cycle. For instance, *P. falciparum* relies on adhesion to RBC surfaces for cell invasion. Administration of RBC-NPs can enclose the pathogens in a layer of nanoparticles, thereby preventing their access into RBCs. Another example is *C. albicans*, which adheres to RBCs to derive iron content as nutrient. Encasing the fungus with RBC-NPs interferes with the nourishment mechanism and provides therapeutic intervention (FIG. 3A).

Enabling Targeted Antibiotic Delivery:

Antibiotic cargoes can be encapsulated in polymeric cores of cell-membrane coated nanoparticles for targeted drug delivery to pathogens. The particles can help concentrate antibiotics to pathogenic bodies, thereby improving the therapeutic efficacy of drugs. In one example, quinine, an intravenous antimalarial, can be encapsulated in polymeric nanoparticles through a double emulsion method. The particles can then be cloaked in RBC membranes to target *P. falciparum*. Such a delivery strategy is expected to better localize drugs to pathogens (FIG. 3B).

Pathogen Isolation and Removal:

The cores in cell membrane cloaked nanoparticles can encapsulate magnetic materials to facilitate the isolation and removal of pathogens from systemic infections. For instance, iron oxide nanoparticles (<10 nm) can be encapsulated in 100 nm polymeric nanoparticles. Following red blood cell membrane cloaking, the nanoparticles can be used to adhere to systemic pathogens such as influenza viruses, *E. coli*, *P. falciparum*, and *C. albicans*. Following administration of these particles, a patients' blood can be passed through a dialysis device, in which magnetic fields can be applied to isolate and remove the pathogenic materials (FIG. 3C).

Pathogen Diagnosis:

Nanoparticle cores with optical properties (such as gold nanoparticles) can be cloaked in biological membranes for pathogen targeting. Following attachment to pathogenic bodies, changes in optical properties, such as shifts in surface plasmon bands, can be monitored. Presence of pathogenic bodies can then be evaluated by observing the optical shifts. Such device can be applied for in vivo as well as in vitro diagnostics (FIG. 3D).

The present invention is further illustrated by the following non-limiting exemplary embodiments:

1. A nanoparticle comprising a polymeric particle core coated with a biological membrane.
2. The nanoparticle of embodiment 1, wherein said biological membrane coating is a cell membrane comprising at least one membrane surface moiety adapted for pathogen-cell adhesion.
3. The nanoparticle of embodiment 2, wherein said membrane surface moiety comprises membrane-bound proteins or glycans.
4. The nanoparticle of embodiment 2, wherein said cell membrane is derived from red blood cells (RBCs).
5. The nanoparticle of embodiment 1, wherein said polymeric particle core encapsulates at least one cargo for targeted drug delivery to pathogens.
6. The nanoparticle of embodiment 5, wherein said cargo is antibiotic.
7. The nanoparticle of embodiment 6, wherein said antibiotic is quinine.
8. The nanoparticle of embodiment 5, wherein said cargo is a magnetic material to facilitate isolation and removal of pathogens from systemic infections.
9. The nanoparticle of embodiment 8, wherein said magnetic material is iron oxide.
10. The nanoparticle of embodiment 5, wherein said polymeric particle core has an optical shift property.
11. The nanoparticle of embodiment 10, wherein said polymeric particle core comprises gold.
12. A method of intervening in an adhering mechanism of a pathogen comprising:
    a) administering the membrane coated nanoparticles of embodiment 1 to host cells under pathogenic assault;
    b) enclosing pathogens in a layer of the nanoparticle;
    c) precluding enclosed pathogen interaction with host cells; and
    d) intervening the pathogen proliferative cycle in the host cells.
13. The method of embodiment 12, wherein said membrane coated nanoparticles are nanoparticles coated with red blood cell membranes (RBC-NPs).
14. The method of embodiment 13, wherein said pathogen is selected from the group consisting of bacterial, virus, and fungus.
15. The method of embodiment 14, wherein said pathogen is influenza virus.
16. The method of embodiment 14, wherein said pathogen is *P. falciparum*.
17. The method of embodiment 14, wherein said pathogen is *C. albicans*.
18. A method of targeted and concentrated drug delivery to a pathogen body comprising administering the membrane coated nanoparticles of embodiment 1 to a pathogenic body so as to localize and target the drug to the pathogen.
19. The method of embodiment 18, wherein said drug is antibiotic.
20. The method of embodiment 18, wherein said membrane coated nanoparticles are nanoparticles coated with red blood cell membranes (RBC-NPs).
21. The method of embodiment 18, wherein said drug is quinine encapsulated in the RBC membrane coated nanoparticles to target *P. falciparum*.
22. A method of facilitating isolation and removal of a pathogen from systemic infections comprising:
    a) administering the membrane coated nanoparticles to a subject in need;
    b) adhering said nanoparticles to a systemic pathogen; and
    c) isolating and removing said pathogen.

23. The method of embodiment 22, wherein said membrane coated nanoparticle encapsulates a magnetic material in the polymeric particle core and coated with red blood cell membranes.

24. The method of embodiment 23, wherein said magnetic material is iron oxide.

25. The method of embodiment 24, wherein a magnetic field is applied in a dialysis device to isolate and remove the pathogen.

26. The method of embodiment 22, wherein said pathogen is selected from the group consisting of influenza virus, *E. coli, P. falciparum, C. albicans*, and other bacteria or fungus.

27. A diagnostic device comprising the membrane coated nanoparticles comprising optical properties for monitoring pathogen targeting.

28. A method of monitoring and diagnosing pathogen targeting comprising:
    a) administering the membrane coated nanoparticles of embodiment 1,
    b) attaching said nanoparticles to a pathogen body, and
    c) monitoring and evaluating optical shifts in the presence said pathogen body attached to said nanoparticles.

REFERENCES

1. Lehmann, F.; Tiralongo, E.; Tiralongo, J., Sialic acid-specific lectins: occurrence, specificity and function. *Cell Mol Life Sci* 2006, 63 (12), 1331-1354.
2. Roberts, D. D., Interactions of respiratory pathogens with host cell surface and extracellular matrix components. *Am J Respir Cell Mol Biol* 1990, 3 (3), 181-186.
3. Pizarro-Cerda, J.; Cossart, P., Bacterial adhesion and entry into host cells. *Cell* 2006, 124 (4), 715-727.
4. Brekke, O. L.; Hellerud, B. C.; Christiansen, D.; Fure, H.; Castellheim, A.; Nielsen, E. W.; Pharo, A.; Lindstad, J. K.; Bergseth, G.; Leslie, G.; Lambris, J. D.; Brandtzaeg, P.; Mollnes, T. E., *Neisseria meningitidis* and *Escherichia coli* are protected from leukocyte phagocytosis by binding to erythrocyte complement receptor 1 in human blood. *Mol Immunol* 2011, 48 (15-16), 2159-2169.
5. Hirst, G. K., Adsorption of Influenza Hemagglutinins and Virus by Red Blood Cells. *J Exp Med* 1942, 76 (2), 195-209.
6. Steck, T. L., The organization of proteins in the human red blood cell membrane. A review. *J Cell Biol* 1974, 62 (1), 1-19.
7. Nicholls, J. M.; Chan, R. W.; Russell, R. J.; Air, G. M.; Peiris, J. S., Evolving complexities of influenza virus and its receptors. *Trends Microbiol* 2008, 16 (4), 149-157.
8. Smith, D. H.; Byrn, R. A.; Marsters, S. A.; Gregory, T.; Groopman, J. E.; Capon, D. J., Blocking of HIV-1 infectivity by a soluble, secreted form of the CD4 antigen. *Science* 1987, 238 (4834), 1704-1707.
9. Kwong, P. D.; Wyatt, R.; Robinson, J.; Sweet, R. W.; Sodroski, J.; Hendrickson, W. A., Structure of an HIV gp120 envelope glycoprotein in complex with the CD4 receptor and a neutralizing human antibody. *Nature* 1998, 393 (6686), 648-659.
10. Arthos, J.; Deen, K. C.; Chaikin, M. A.; Fornwald, J. A.; Sathe, G.; Sattentau, Q. J.; Clapham, P. R.; Weiss, R. A.; McDougal, J. S.; Pietropaolo, C.; et al., Identification of the residues in human CD4 critical for the binding of HIV. *Cell* 1989, 57 (3), 469-481.
11. Rosenthal, L., Agglutinating Properties of *Escherichia coli*: Agglutination of Erythrocytes, Leucocytes, Thrombocytes, Spermatozoa, Spores of Molds, and Pollen by Strains of *E. Coli*. *J Bacteriol* 1943, 45 (6), 545-550.
12. Leach, J. L.; Garber, S. A.; Marcon, A. A.; Prieto, P. A., In vitro and in vivo effects of soluble, monovalent globotriose on bacterial attachment and colonization. *Antimicrob Agents Chemother* 2005, 49 (9), 3842-3846.
13. Shenkman, B.; Rubinstein, E.; Cheung, A. L.; Brill, G. E.; Dardik, R.; Tamarin, I.; Savion, N.; Varon, D., Adherence properties of *Staphylococcus aureus* under static and flow conditions: roles of agr and sar loci, platelets, and plasma ligands. *Infect Immun* 2001, 69 (7), 4473-4478.
14. Heilmann, C.; Niemann, S.; Sinha, B.; Herrmann, M.; Kehrel, B. E.; Peters, G., *Staphylococcus aureus* fibronectin-binding protein (FnBP)-mediated adherence to platelets, and aggregation of platelets induced by FnBPA but not by FnBPB. *J Infect Dis* 2004, 190 (2), 321-329.
15. Duraisingh, M. T.; Maier, A. G.; Triglia, T.; Cowman, A. F., Erythrocyte-binding antigen 175 mediates invasion in *Plasmodium falciparum* utilizing sialic acid-dependent and -independent pathways. *Proc Natl Acad Sci USA* 2003, 100 (8), 4796-4801.
16. Kappe, S. H.; Noe, A. R.; Fraser, T. S.; Blair, P. L.; Adams, J. H., A family of chimeric erythrocyte binding proteins of malaria parasites. *Proc Natl Acad Sci USA* 1998, 95 (3), 1230-1235.
17. Adams, J. H.; Sim, B. K.; Dolan, S. A.; Fang, X.; Kaslow, D. C.; Miller, L. H., A family of erythrocyte binding proteins of malaria parasites. *Proc Natl Acad Sci USA* 1992, 89 (15), 7085-7089.
18. Calderone, R.; Suzuki, S.; Cannon, R.; Cho, T.; Boyd, D.; Calera, J.; Chibana, H.; Herman, D.; Holmes, A.; Jeng, H. W.; Kaminishi, H.; Matsumoto, T.; Mikami, T.; O'Sullivan, J. M.; Sudoh, M.; Suzuki, M.; Nakashima, Y.; Tanaka, T.; Tompkins, G. R.; Watanabe, T., *Candida albicans*: adherence, signaling and virulence. *Med Mycol* 2000, 38 Suppl 1, 125-137.
19. Hu, C. M.; Zhang, L.; Aryal, S.; Cheung, C.; Fang, R. H., Erythrocyte membrane-camouflaged polymeric nanoparticles as a biomimetic delivery platform. *Proc Natl Acad Sci USA* 2011, 108 (27), 10980-10985.
20. Cleary, J.; Lai, L. C.; Shaw, R. K.; Straatman-Iwanowska, A.; Donnenberg, M. S.; Frankel, G.; Knutton, S., Enteropathogenic *Escherichia coli* (EPEC) adhesion to intestinal epithelial cells: role of bundle-forming pili (BFP), EspA filaments and intimin. *Microbiology* 2004, 150 (Pt 3), 527-538.
21. Boyle, M. J.; Wilson, D. W.; Richards, J. S.; Riglar, D. T.; Tetteh, K. K.; Conway, D. J.;
Ralph, S. A.; Baum, J.; Beeson, J. G., Isolation of viable *Plasmodium falciparum* merozoites to define erythrocyte invasion events and advance vaccine and drug development. *Proc Natl Acad Sci USA* 2010, 107 (32), 14378-14383.
22. Heidenreich, F.; Dierich, M. P., *Candida albicans* and *Candida stellatoidea*, in contrast to other *Candida* species, bind iC3b and C3d but not C3b. *Infect Immun* 1985, 50 (2), 598-600.

The invention claimed is:

1. A method of facilitating isolation and removal of a parasitic protozoan that causes malaria from systemic infections comprising:
    a) administering to a subject in need a nanoparticle consisting of an inner core comprising a biocompatible or a synthetic material selected from the group consisting of poly(lactic-co-glycolic acid) (PLGA), polylactic acid (PLA), polyglycolic acid (PGA), polycaprolactone (PCL), polylysine, and polyglutamic acid, an outer surface consisting of red blood cell membrane, and a magnetic material encapsulated in said inner core;

b) adhering said nanoparticle to said parasitic protozoan that causes malaria; and c) isolating and removing said parasitic protozoan that causes malaria from said subject, wherein said method does not comprise administering quinine to said subject.

2. The method of claim 1, wherein the magnetic material is iron oxide.

3. The method of claim 1, wherein a magnetic field is applied in a dialysis device to isolate and remove the parasitic protozoan that causes malaria.

4. The method of claim 1, wherein the subject is a mammal.

5. The method of claim 4, wherein the mammal is a human.

6. The method of claim 1, wherein the inner core supports the outer surface.

7. The method of claim 1, wherein the nanoparticle has a diameter from about 10 nm to about 10 μm.

8. The method of claim 1, wherein the nanoparticle substantially lacks hemoglobin of the red blood cell from which the cellular membrane is derived.

9. The method of claim 1, wherein the inner core of the nanoparticle consists of PLGA and the encapsulated magnetic material, and the outer surface of the nanoparticle consists of a plasma membrane derived from a red blood cell.

10. The method of claim 1, wherein the nanoparticle substantially lacks immunogenicity to the subject.

11. The method of claim 1, wherein the parasitic protozoan is *P. falciparum, P. malariae, P. ovale, P. vivax* or *P. knowlesi*.

12. The method of claim 11, wherein the malaria is severe malaria, uncomplicated malaria or cerebral malaria.

* * * * *